(12) United States Patent
Paderni (10) Patent No.: US 6,491,682 B2
(45) Date of Patent: *Dec. 10, 2002

(54) APPARATUS FOR EXTRACTING FLUIDS

(75) Inventor: Valter Paderni, Lignano Sabbiadoro (IT)

(73) Assignee: CRB Nederland B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,422

(22) PCT Filed: Aug. 12, 1997

(86) PCT No.: PCT/EP97/04382

§ 371 (c)(1),
(2), (4) Date: Apr. 20, 1999

(87) PCT Pub. No.: WO98/07460

PCT Pub. Date: Feb. 26, 1998

(65) Prior Publication Data

US 2001/0025170 A1 Sep. 27, 2001

(30) Foreign Application Priority Data

Aug. 16, 1996 (IT) .......................... UD96A0161

(51) Int. Cl.⁷ ................................ A61M 1/00
(52) U.S. Cl. ...................... 604/541; 604/317
(58) Field of Search .................. 604/540, 541, 604/317, 542, 318, 319, 332, 336, 337, 338, 133, 149, 313

(56) References Cited

U.S. PATENT DOCUMENTS

| | | | | |
|---|---|---|---|---|
| 3,777,757 A | * | 12/1973 | Gray et al. | 604/96 |
| 4,228,798 A | * | 10/1980 | Deaton | 604/49 |
| 4,769,017 A | * | 9/1988 | Fath et al. | 604/283 |
| 5,053,025 A | | 10/1991 | Knippscheer | |
| 5,073,164 A | * | 12/1991 | Hollister et al. | 604/43 |
| 5,156,602 A | * | 10/1992 | Steffler | 604/319 |
| 5,356,373 A | | 10/1994 | Dracker | |
| 5,599,331 A | * | 2/1997 | Hemstreet et al. | 604/317 |
| 5,620,008 A | * | 4/1997 | Shinar et al. | 128/764 |

FOREIGN PATENT DOCUMENTS

WO          9203180          3/1992

* cited by examiner

Primary Examiner—Brian L. Casler
Assistant Examiner—Kevin C. Sirmons
(74) Attorney, Agent, or Firm—Greer, Burns & Crain, Ltd.

(57) ABSTRACT

An apparatus (1) for extracting fluids from a body tissue or organ having an aperture, including a seat (26) for positioning said tissue, and a pressure membranes (17,22) for applying pressure to said tissue while leaving said tissue aperture open for the exit of said fluids. The surface (23) of the supporting surface of the tissue is shaped as a funnel or cone, so that the apex is directed downward and the base (29) delimits the supporting surface of the tissue; the apex region being constituted by a hollow cylinder (22) in order to allow the passage of the umbilical cord of a placenta or of the vessel for the drainage of fluids from the placenta or organ or tissue; the supporting surface being provided so as to avoid producing obstructions or collapse of the surface vessels of the placenta or organ or tissue, so as to avoid hindering the flow of blood or fluids

66 Claims, 7 Drawing Sheets

APPARATUS FOR EXTRACTING FLUIDS

BACKGROUND OF THE INVENTION

The present invention relates to an apparatus for extracting fluids, such as blood or other fluids from a placenta or from other human or animal organs or tissues.

The apparatus according to the invention is used mainly in the biological, medical and veterinary field both for diagnostic and therapeutic purposes and for research purposes, for the extraction of blood or other fluids from the placenta or another organ or tissue to be used subsequently as a source of cells, molecules or other.

In the biological, medical and veterinary fields it is necessary to collect fluids, particularly blood, from organs or tissues or containers in general, both for diagnostic and therapeutic purposes and for research purposes. Two non-limitative examples are: 1. the collection of blood from masses of tumoral tissue, since the blood contained in the tumoral tissue is potentially useful for therapeutic purposes after appropriate treatment; 2. the collection of blood from the placenta during childbirth directly after cutting the umbilical cord. In this second case, the blood is useful since it contains stem cells, which are hematopoietic precursor cells, that is to say, cells which are capable of reconstituting the hematopoietic system and therefore can be used, if the need arises, for transplanting to the same donor or to another compatible recipient.

The procedures currently used to collect placental blood from an umbilical cord are described hereinafter as a typical example of the recovery of fluids from an organ; it is important to note that the reference to this practice is not limitative and is merely an example of situations in which it is necessary to collect blood or another fluid from tissues, organs or other containers in general.

Placental blood from the umbilical cord is collected because it contains hematopoietic stem cells which can be used for transplants. To allow the collected blood and therefore the recovered cells to be truly and successfully usable, the following conditions must be met: 1. the largest possible amount of blood, that is to say, the highest possible number of cells, must be recovered; 2. the collected blood, which is fetal in origin, must not be contaminated by foreign cell populations, such as for example maternal cells; 3. during collection, contact of the blood with the outside (air or other potentially contaminated objects) must be minimized, or the collection procedure must occur in sterile conditions, possibly in a closed environment; 4. the possibility of human error must be minimized.

Steps of Collection a. Before Expulsion of the Placenta.

Blood is currently extracted from the placenta in the medical field, both for diagnostic and therapeutic purposes and for research purposes, as follows: during childbirth, directly after the expulsion of the newborn child, the umbilical cord is closed (clamped) in two points and cut in a point which is intermediate between the two closure points. After cutting, the cut end of the umbilical cord which is connected to the placenta protrudes freely from the mother's vagina and is available for collection operations. Typically, blood is collected in the period between the cutting of the umbilical cord and expulsion of the placenta. During this period, the flow of blood is ensured by the pressure generated by uterine contractions, which by compressing the placenta facilitate the outflow of blood through the umbilical cord.

b. After Expulsion of the Placenta.

Only a small number of authors reports collection procedures which provide for cord blood collection after expulsion of the placenta by placing the placenta on a frame and collecting the blood by gravity. The limited use of collection after expulsion of the placenta is certainly due to the low yield of collection by gravity and to difficulty in handling the placenta, especially when the sterility of the collected blood must be guaranteed.

Collection Systems

Collection of placental blood from the umbilical cord in the medical field, both for diagnostic and therapeutic purposes and for research purposes, is currently performed with systems which can be traced back to two categories: "open-circuit" systems and "closed-circuit" systems. Both systems are used for collection both before and after expulsion of the placenta.

a. "Open-circuit" Systems

"Open-circuit" systems collect placental blood from the cut umbilical cord in containers which contain anticoagulant. This collection is performed by making the blood flow out directly into the collection container without connecting the end portion of the cord, which is placed loosely at the inlet of the container.

Advantages

The main advantage of this system is the absence of resistances to flow, since there are no bottlenecks or sudden decreases in cross-section of the cord and of its vessels.

A second advantage is that the three vessels which are present in the umbilical cord are simultaneously pervious.

Another advantage of the system is the possibility to express the umbilical cord during collection.

Disadvantages

Various scientific papers have demonstrated that "open-circuit" systems do not ensure sterility and are in fact associated with a particularly high incidence of microbial contaminations. The cut end portion of the umbilical cord in fact has a loose consistency, and since it is simply rested on the inlet of the collecting container it can easily escape from it, consequently contaminating said end portion in addition to losing blood, which contaminates the outside environment.

Furthermore, the system inherently (being an "open" system) collects both the blood that flows out of the vessels of the cord and potentially contaminated liquids which flow along the outer surface of the umbilical cord; in particular, the maternal blood which is abundantly present along the outer surface of the placenta flows along the cord and mixes with the blood of the umbilical cord.

This collection system furthermore exposes the blood to the air of the outside environment, thus facilitating contaminations from microorganisms which are present in the outside environment.

Another drawback is the constant need for an operator assigned to keeping the umbilical cord in the correct position, particularly if repeated maneuvers for expressing and cleaning the cord are performed.

b. "Closed-circuit" Systems

Collection is performed by venipuncture of the cut and clamped end of the umbilical cord, after accurately disinfecting the entry point of the needle. The blood is collected in one or more syringes or in donation pouches.

Advantages

With respect to "open-circuit" systems, "closed-circuit" systems reduce the risks of microbial contamination of the collected blood and do not require continuous cleaning and disinfection of the cord.

Another advantage is reduction of the contamination of the sample with maternal blood or other liquids which flow along he outer surface of the cord.

Disadvantages

"Closed-circuit" systems entail handling needles and therefore expose the operators to the risk of accidental punctures.

Furthermore, the needle inserted in the umbilical vein is not stably fixed to it and can easily come loose, also in view of the highly dynamic nature of childbirth; this problem is particularly felt if collection is continued even after expulsion of the placenta. Accordingly, the continuous presence of an operator is required to ensure the correct placement of the needle during the various steps of collection.

If the needle leaves its seat, blood contaminations and accidental punctures of the operator are possible, and repetition of venipuncture is required in order to continue collection.

Owing to the limited cross-section of two of the three vessels of the umbilical cord (the arteries), collection is feasible only on one vessel (the vein), consequently reducing the collection potential.

The flow of blood is hindered by the sudden decrease in cross-section (the needle, no matter how large, can never have the same cross-section as the umbilical vein).

The needle is inserted in an intermediate segment of the umbilical cord, upstream of the closure region; stasis of the blood downstream of the insertion point, with a consequent tendency to clotting, is thus inevitable; moreover, the blood which remains downstream of the insertion point is not recovered.

WO-A-92/03180 discloses an apparatus for extracting blood form a placenta and umbilical cord having a support assembly for holding the placenta with umbilical cord and a pressure exerting device. The support assembly includes a rotatable conical receptacle adapted to receive and hold the placenta.

U.S. Pat. No. 5,053,025 discloses an apparatus for extracting blood from a placenta and an umbilical cord, including a stationary frame with a rotatable carriermounted thereto and a balloon which is inflated by a compressor, in order to press the placenta.

SUMMARY OF THE INVENTION

An aim of the present invention is to provide an apparatus for extracting fluids, particularly blood, from a placenta or another organ or tissue, whether human or animal, both for diagnostic and therapeutic purposes and for research purposes, overcoming the drawbacks of the prior art systems.

An object of the present invention is to provide an apparatus which does not require particular experience or training for its operation.

A further object of the present invention is to provide an apparatus safe in use and free from critical points and risks of error.

A further object of the present invention is to provide an apparatus enabling a health operator with normal experience of performing the entire procedure without risks. Still a further object of the present invention is to provide an apparatus ensuring optimum yield, repeatable over time.

Still a further object of the present invention is to provide an apparatus that limits contamination of the environment with blood and other potentially infected material.

The above aims and other aims that will become apparent to those skilled in the art, are achieved by an apparatus as claimed in the appended claims.

BRIEF DESCRIPTION OF THE DRAWINGS

Further characteristics and advantages of the invention will become apparent from a reading of the detailed description of a preferred but not exclusive embodiment of the invention illustrated only by way of a non-limiting example in the accompanying drawings, wherein.

DESCRIPTION OF THE PREFERRED EMBODIMENTS

The exemplifying and non-limitative description of the apparatus given hereinafter relates to its application to the extraction of blood from the placenta through the umbilical cord after expulsion of the placenta. The apparatus according to the invention can of course be used for collecting blood or other fluids even from other organs or tissues.

Figure 7:
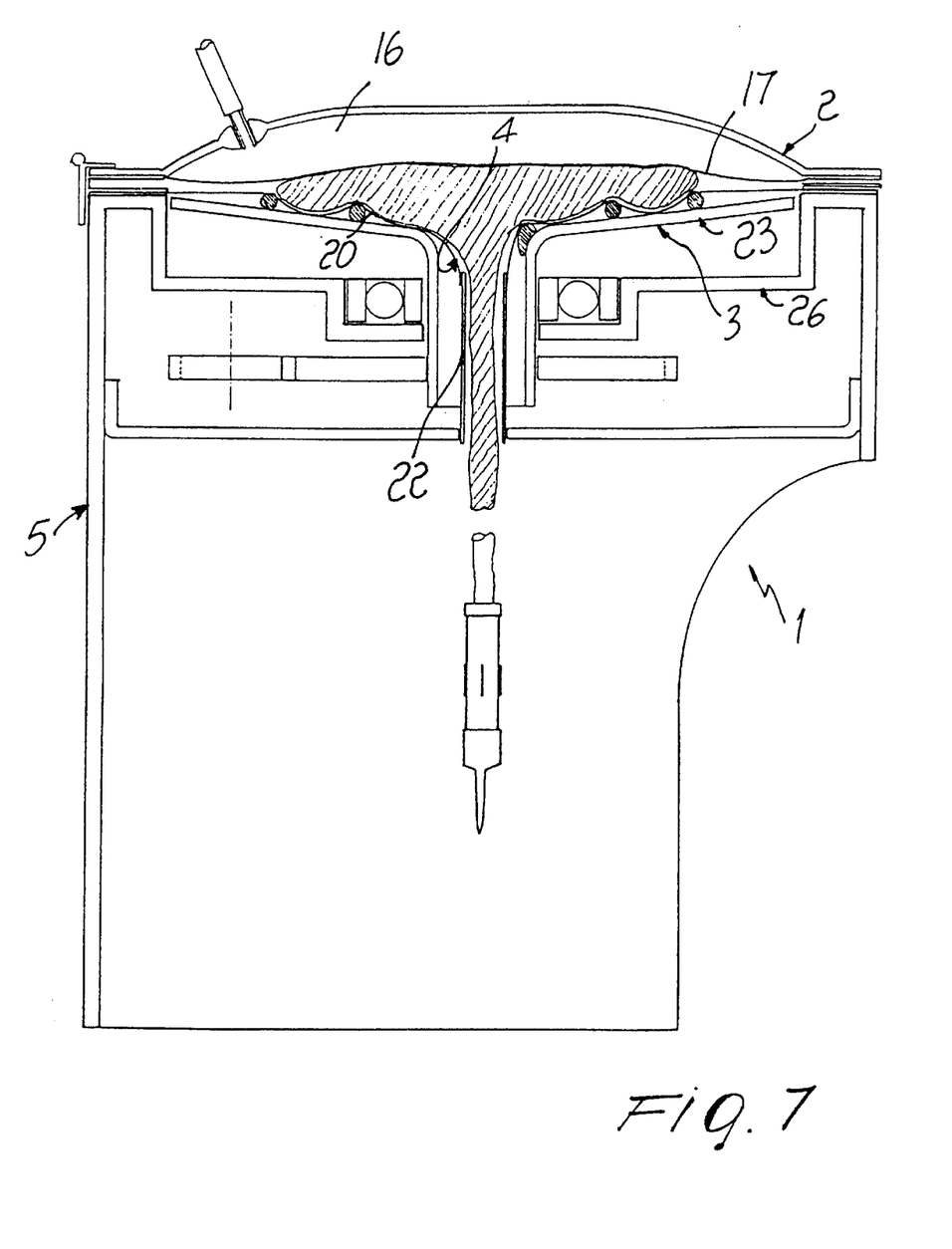
FIG. 7 is a schematic general view of the apparatus for applying pressure to the placenta or organ or tissue and optionally to the proximal portion of the umbilical cord.

The apparatus according to the invention, generally designated by the reference numeral 1, as illustrated in FIG. 7, is composed of four parts:

An upper part 2, suitable to apply uniform or localized, pulsed or continuous mechanical pressure on the upper part of the placenta.

Figure 1:
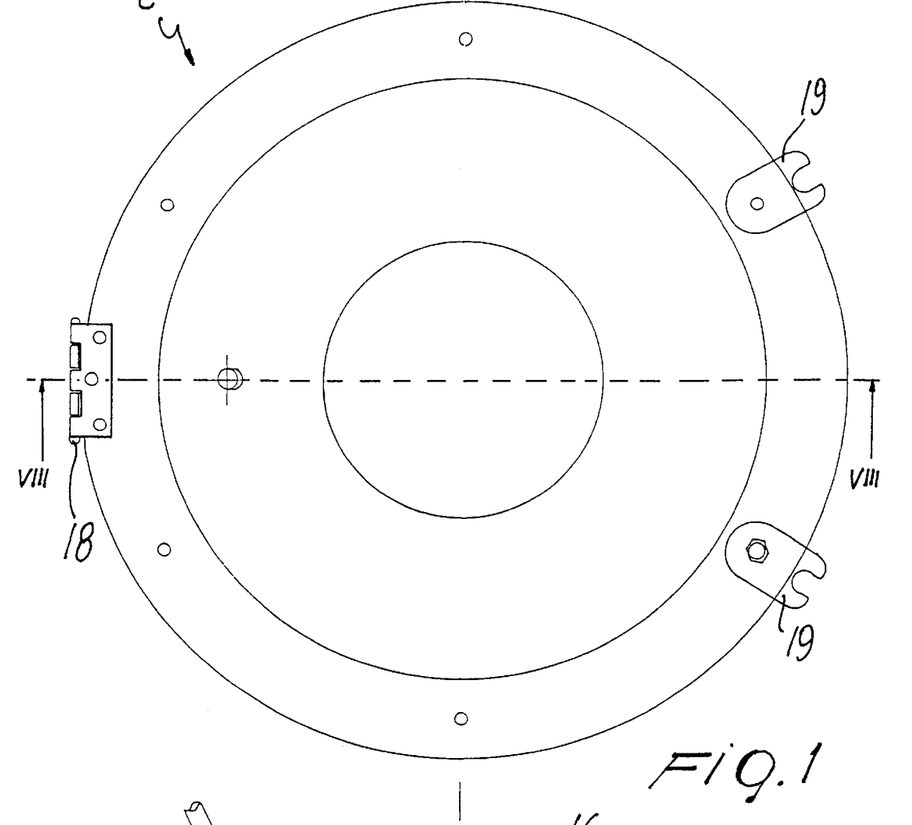
FIG. 1 is a view of the upper part, meant to apply uniform or localized, pulsed or continuous mechanical pressure on the maternal surface, hereinafter referenced as the upper surface of the placenta.
Figure 8:
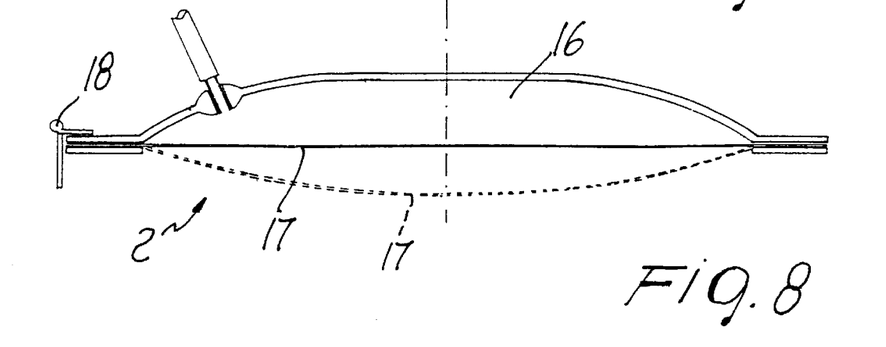
FIG. 8 is a section view according to the section line VIII—VIII of FIG. 1.

The upper part of the exemplifying system described here FIG. 1 is constituted by a hollow surface of suitable size and shape, made of metal or plastic, polymers or other material suitable for the purpose, which is meant to form a cavity 16 which is closed and sealed by virtue of the suitable positioning of a membrane 17 made of an elastic material, which can be rubber, silicone, polymers or other material. The pressure inside the chamber is changed and adjusted by means of a manual, electric, mechanical or other system. The pressure variation inside the chamber produces curving of the rubber membrane, which can thus assume a concave, plane or convex shape or the shape of an object placed in direct contact therewith. The surface of the membrane can be smooth or discontinuously shaped and may also have the purpose of transmitting uniform or localized, continuous or pulsed, radially or centripetally orientated mechanical pressure on the upper surface of the placenta, said pressure being generated by means of a suitable device. The upper part is connected to the other parts of the machine by virtue of a hinge or joint mechanism or other system 18. A locking system 19 of the screw, pin or other type ensures locking of the upper part in the intended position.

Figure 2:
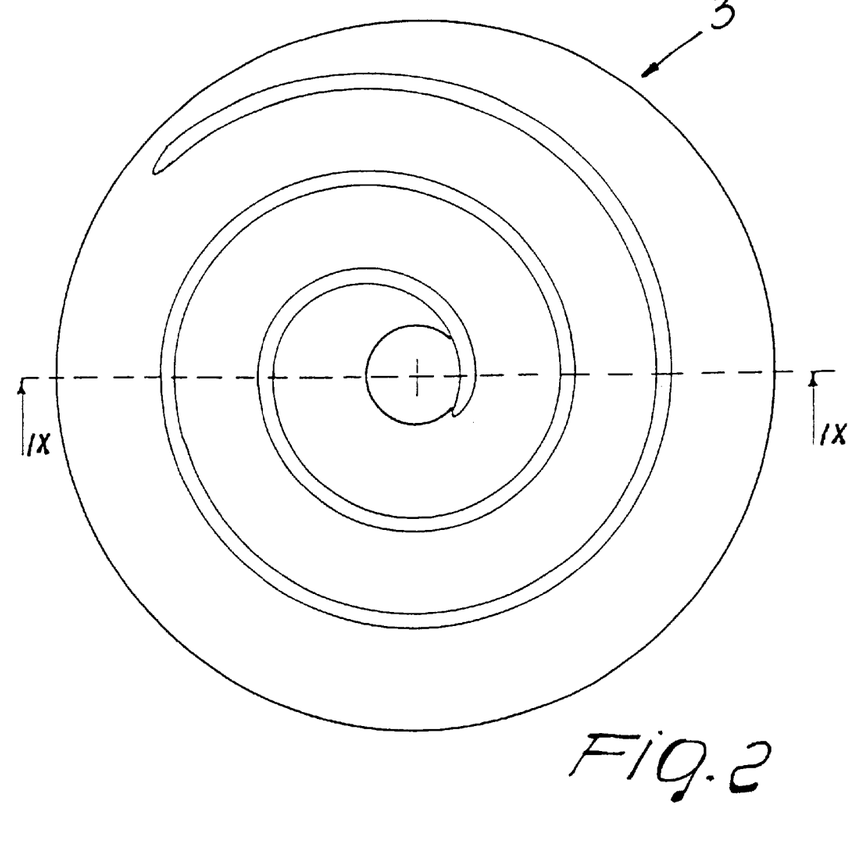
FIG. 2 is a view of a rotating lower cone, which is meant to rest and apply uniform or localized, pulsed or continuous mechanical pressure in a radial or centripetal direction on the fetal surface, hereinafter referenced as the lower surface of the placenta, and on the initial portion of the umbilical cord.

A lower part 3 is adapted to support and apply uniform or localized, pulsed or continuous, radially or centripetally orientated mechanical pressure to the lower surface of the placenta and to the portion of the umbilical cord.

Figure 9:
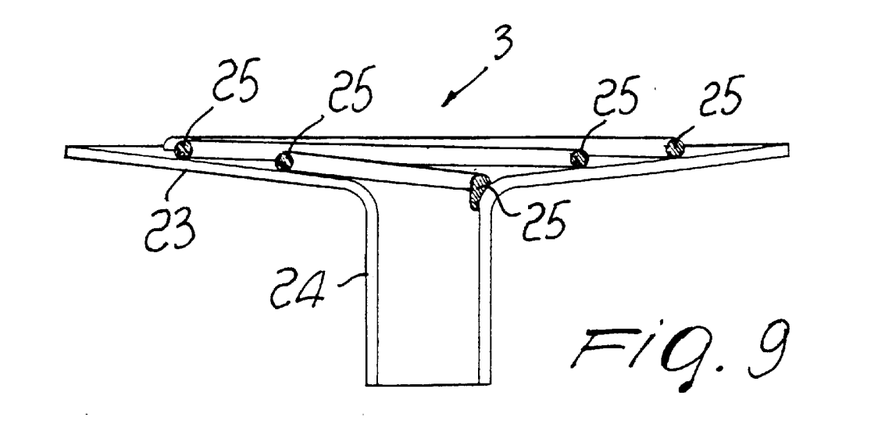
FIG. 9 is a section view according to the section line IX—IX of FIG. 2.

The lower part of the exemplifying system described herein FIG. 2 is constituted by a conical or funnel-shaped element 23 of appropriate size which ends, at its apex, with a tube 24 having a cross-section which is suitable to allow the passage of an optional system for connecting the umbilical cord and the collecting container. The end tube is in turn inserted and locked in a ball or roller bearing or a bushing, thus allowing the cone to rotate freely about its generating axis. The bearing or other system is in turn stably fixed to the machine body by virtue of a suitable support or seat. The inner surface of the cone has one or more ridges with a suitable cross-section 25 which have a spiral or helical or epicycloidal arrangement and start in the central region of the cone, proximate to the beginning of the cylindrical or hollow part.

Figure 5:
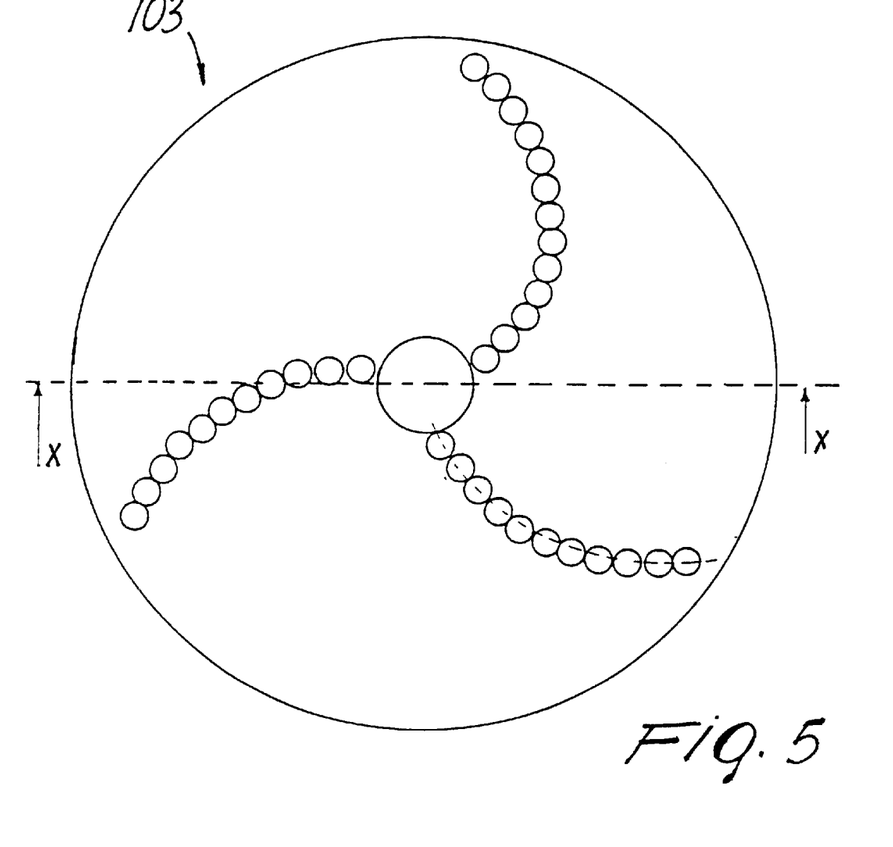
FIG. 5 is a view of a variation of the lower rotating cone, which is meant to provide support and apply uniform or localized, pulsed or continuous mechanical pressure with a radial or centripetal or random orientation on the lower surface of the placenta and on the initial portion of the umbilical cord.
Figure 10:
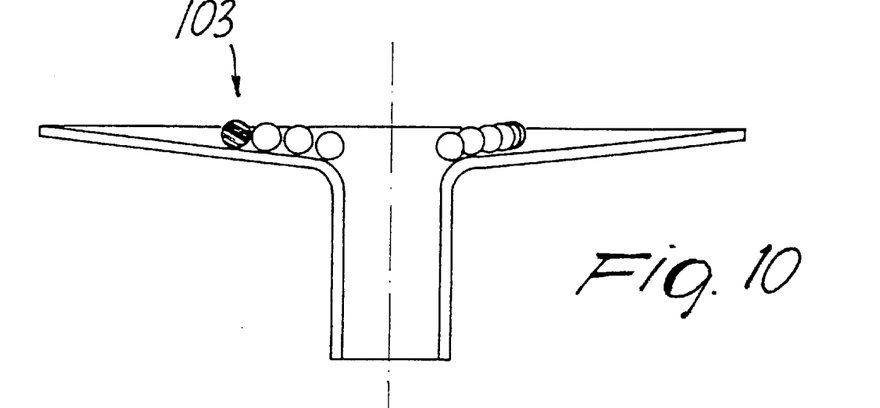
FIG. 10 is a section view according to the section line X—X of FIG. 5.

A second exemplifying and non-limitative variation of the lower part 103, shown in the hypothetical representation of FIG. 5, is constituted by a series of balls with an eccentric axis or cams which are arranged so as to roll on the supporting membrane and are rigidly coupled to the lower cone by virtue of an appropriately shaped (straight, spiral, etc.) axis. This variation ensures a pressure from above which is pulsed and concentrated on the lower surface of the placenta, eliminating radial traction on said placenta.

Figure 6:
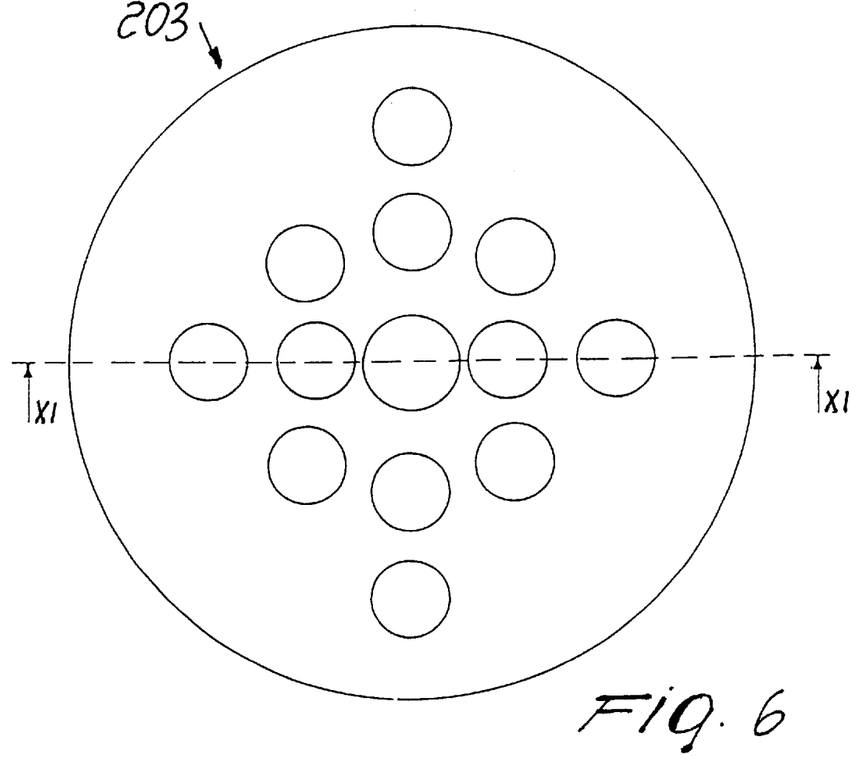
FIG. 6 is a view of a variation of the lower rotating cone, which is meant to provide support and apply uniform or localized, pulsed or continuous, radial or centripetal or random mechanical pressure on the lower surface of the placenta and on the initial portion of the umbilical cord.
Figure 11:
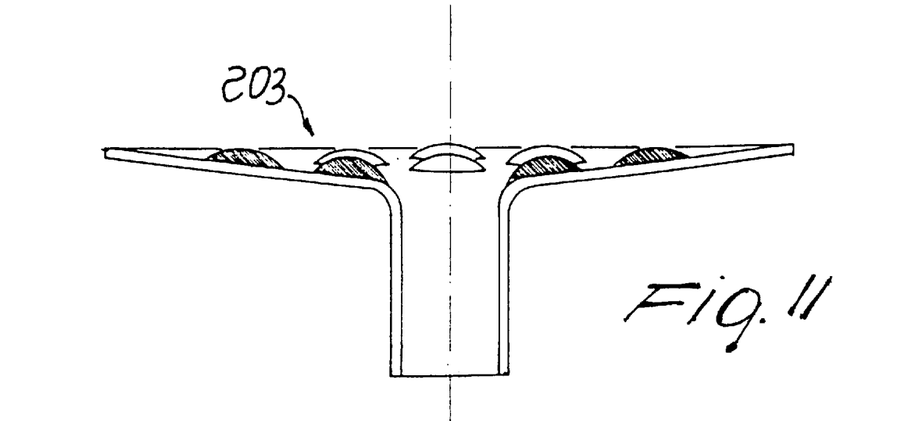
FIG. 11 is a section view according to the section line XI—XI of FIG. 6.

Another exemplifying and non-limitative variation 203, shown in FIG. 6, is constituted by raised portions of suitable size and shape which are suitable to transmit localized and tangentially-orientated pressures to the lower surface of the placenta.

A combination of the above variations is also possible to ensure axial thrusts with different vectors on the placenta. The lower cone can be made of plastic or metal or other material suitable for this purpose.

Figure 3:
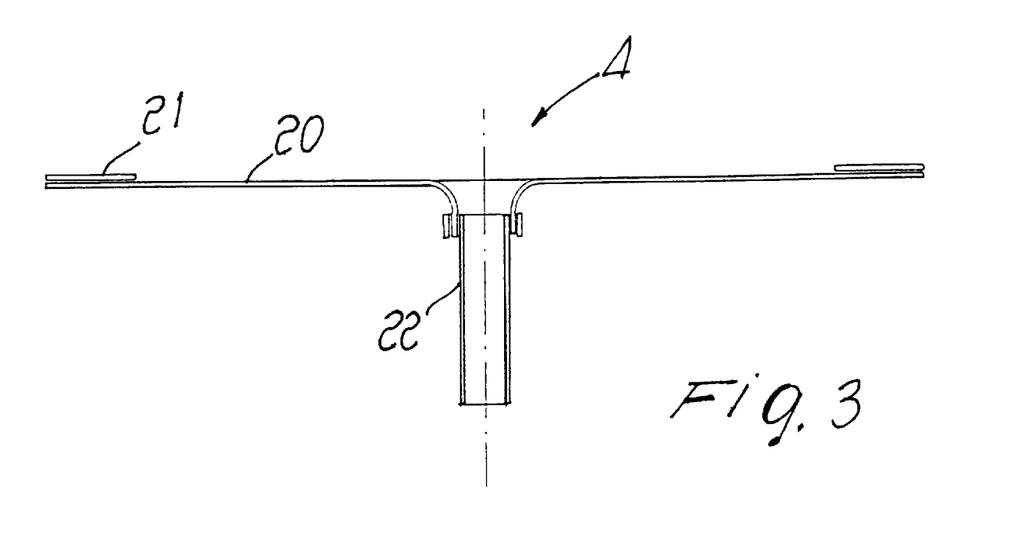
FIG. 3 is a view of the supporting membrane made of elastic material, which is meant to provide support and transmit uniform or localized, pulsed or continuous mechanical pressure, generated by the lower cone, in a radial or centripetal or random orientation, to the lower surface-of the placenta and to the initial portion of the umbilical cord.

A supporting membrane 4 is made of elastic material, which acts as a surface for support and transmission of uniform or localized, pulsed or continuous, radially or centripetally orientated mechanical pressure on the lower surface of the placenta.

The supporting membrane (FIG. 3) in the exemplifying system described herein is constituted by an element 20 which has a round shape and a suitable diameter and thickness, is made of elastic material such as rubber, silicone, polymers or other material suitable for the purpose, and is rigidly coupled to the machine body by virtue of a ring 21. In the central part, an extension of said membrane or a tube 22 made of plastic or other suitable material fixed to the membrane and rigidly coupled to the machine body by virtue of a bracket 28 allows the accommodation and passage of the umbilical cord and of an optionel connecting system. In the illustrated example, the membrane is arranged so that it can rest with a suitable tension on the spiral ridge of the lower cone. The tension of the membrane is adjusted so as to avoid creating concentrated loads or occlusions of the vessels of the placenta. In order to optimize this tension, a membrane of suitable consistency and thickness is used. The function of the supporting membrane is to transmit the uniform or localized, pulsed or continuous, radially or centripetally or randomly orientated mechanical pressure generated by the movement of the lower cone. Another function of the supporting membrane is to eliminate the lateral and tangent traction of said spiral. optionally, an appropriate lubricant, such as talc, oil or other minimizes friction between the membrane and the lower cone.

Figure 4:
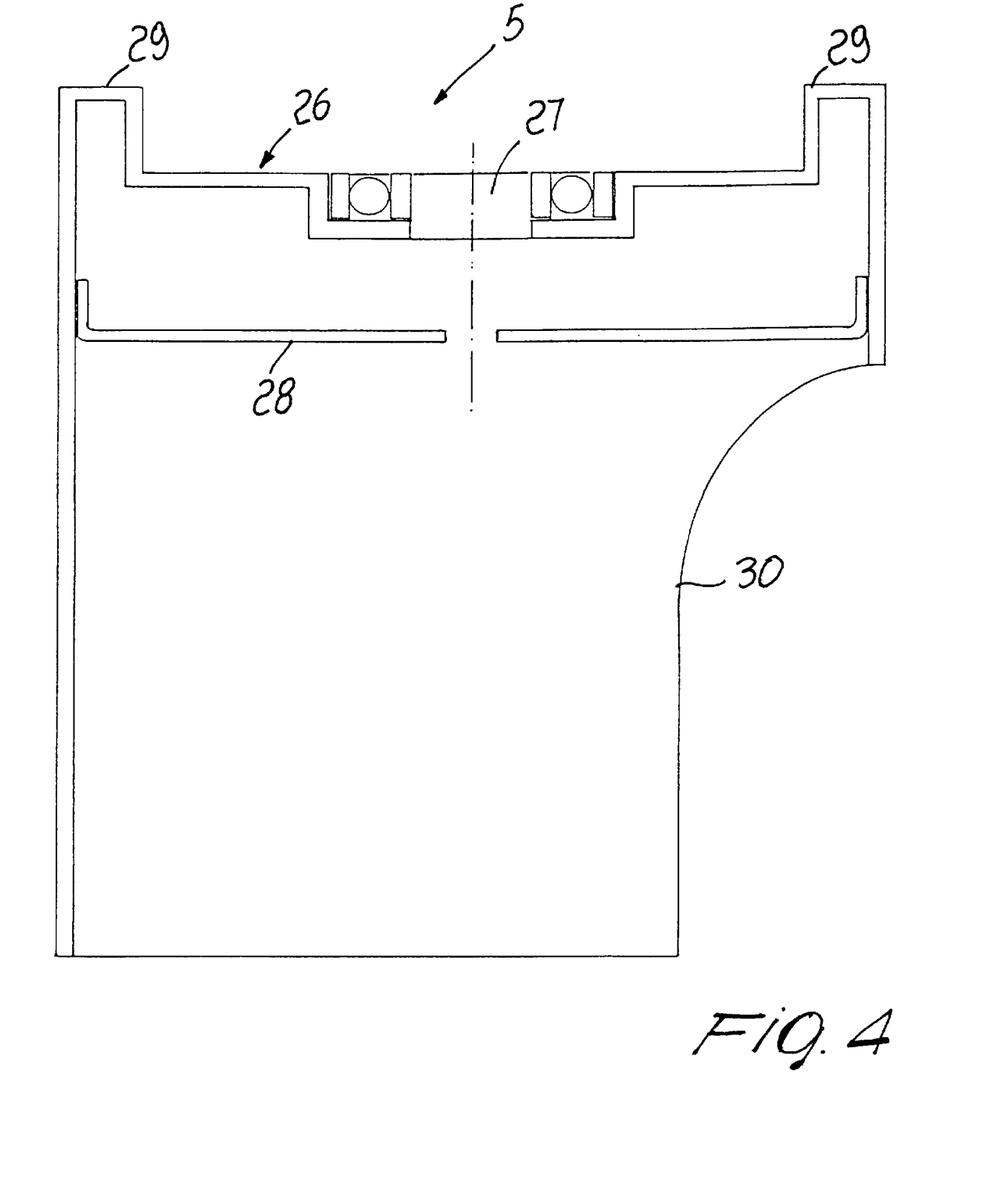
FIG. 4 is a view of the machine body, which is meant to provide support and connect the upper part, the lower resting cone, the supporting membrane, and any mechanical or pneumatic or electric or other elements which are an integral part of the machine.

A machine body 5 acts as support and connection between the upper part, the lower element, the supporting membrane and any mechanical or pneumatic or electric or other elements which are an integral part of the machine.

The machine body is constituted by a supporting frame of appropriate shape and size which is made of metal, plastic or other suitable material and has the function of supporting, connecting and positioning the upper part, the lower element, the supporting membrane and the mechanical or pneumatic or electric or other elements which are an integral part of the machine. In the drawing (FIG. 4), which is a non-limitative example, there is a lower cone seat 26, a lower cone bearing or bushing seat 27, a bracket or support for the lower part of the supporting membrane 28, a base for fixing the supporting membrane 29 and an access to the lower part of the machine 30.

The apparatus described up to now, shown schematically in FIG. 7, is used to apply pressure to the placenta or organ or tissue when it become available, that is to say, in the case of the placenta, after expulsion. The placenta, possibly contained in a suitable container with soft walls with an absorbent inner surface and an impermeable outer surface, such as to not hinder drainage and have a containment and protection function, is placed on the supporting membrane 20 so that the maternal surface, hereinafter termed upper surface, is directed upward, and so that the fetal surface, hereinafter termed lower surface, is directed downward. The umbilical cord, which derives from the lower surface of the placenta, is accommodated, in its initial segment, in the opening of the tube 22 or in the extension of the membrane, whilst its end segment, which has an appropriate length, is connected to a collecting system of the open-circuit or closed-circuit type. The ideal configuration provides for the connection of the end segment of the umbilical cord by virtue of a closed-circuit connecting system which does not compress or in any case does not compromise the flow of blood, keeping open all the vessels located in the umbilical cord, and simultaneously ensures isolation of the sample from the outside environment and is practical and safe in use. In this first configuration, the machine already allows collection of the placental blood by gravity, since an accommodation of this kind allows drainage and does not create occlusions on the surface vessels of the lower part of the placenta. The upper part of the machine, which has been kept open up to now to allows position the placenta on the supporting membrane, is closed and fixed by virtue of appropriate systems. The pressure applied by the membrane in the inactive position solely by closing the upper part, or the pressure generated by a pneumatic, electric or other system inside the sealed chamber is transmitted to the upper surface of the placenta by means of the elastic membrane 17. In this configuration, the drainage effect caused by the position of the placenta is improved by an increase in pressure which is transmitted from the upper surface of the placenta to the internal vessels involved in the drainage. At this point, a uniform or localized, pulsed or continuous, radially or centripetally or randomly orientated mechanical pressure is applied to the lower surface of the placenta; said pressure is generated by the rotary movement of the spiral of the lower cone 26 or by another system and transmitted through the supporting membrane. The combined effect of the two possible pressure application systems described above ensures a high yield in collection which cannot be achieved with the systems and procedures currently used.

The fluid extraction system according to the invention is practical, simple and safe to use; the entire operation is brief, does not require particularly training or skill and does not require the constant presence of an operator.

What is claimed is:

1. An apparatus for extracting fluids from a body tissue having an aperture, the apparatus comprising a seat adapted to position the tissue; and a pressure means for applying pressure to the tissue while leaving said tissue aperture open for the exit of said fluids, wherein said pressure means comprise a plurality of membranes adapted to substantially surround said tissue, said plurality of membranes including at least one elastic membrane.

2. The apparatus according to claim 1, wherein said elastic membrane is stretched on a rigid supporting frame.

3. The apparatus according to claim 2, wherein said rigid supporting frame is hinged to a case body adapted to contain said pressure means; said frame being adapted to be left open in an inactive position, at right angles to a supporting surface adapted to support the tissue, or closed, in an active position, parallel to the supporting surface; wherein, in said closed position, a plane for connecting the elastic membrane to the frame reaches beyond a protrusion profile of the tissue that rests on the supporting surface, thus leaving a central part of the elastic membrane free to act on said tissue and thus deform and compress the tissue, so that the tissue protrudes from the supporting surface to a different extent.

4. The apparatus according to claim 3, wherein said rigid frame is coupled to the elastic membrane so as to delimit a hermetically closed space, which is connected to a pressure system for applying pressure inside said space.

5. The apparatus according to claim 3, wherein the supporting surface is constituted by a circular flat surface which has a central hole whose size is suitable for the passage of a tissue vessel for draining fluids.

6. The apparatus according to claim 5, further comprising a connector adapted to connect to said vessel and a container adapted to collect the fluid, so as to form a closed collection system which allows transfer of the fluid from the tissue to the container by means of a closed system.

7. The apparatus according to claim 3, wherein at least a portion of the supporting surface is shaped substantially as a cone, so that an apex of the cone is directed downward and a base of the cone delimits the supporting surface; the apex being constituted by a hollow cylinder in order to allow the passage of an umbilical cord of a placenta or of a vessel for the drainage of fluids from the placenta or organ or tissue; the supporting surface being provided so as to avoid producing obstructions or collapse of surface vessels of the placenta or organ or tissue, so as to avoid hindering the flow of blood or fluid.

8. The apparatus according to claim 7, wherein the supporting surface has ridges which have a substantially spiral shape and start in the central region of the cone, proximate to the beginning of the hollow cylinder.

9. The apparatus according to claim 3, wherein the supporting surface is free to rotate about a central axis.

10. The apparatus according to claim 3, wherein the supporting surface has raised portions.

11. The apparatus according to claim 3, wherein the supporting surface has balls or cams which are fixed to the supporting surface, below a portion of the pressure means and can rotate freely about their own axis; said balls or cams being moved by friction between a surface of the balls or cams and said portion of the pressure means.

12. The apparatus according to claim 3, wherein the pressure is applied in a connecting part between a supporting membrane and a cylinder for containing an umbilical cord or outflow vessel for fluids and along said cylinder for containing the outflow vessel.

13. The apparatus according to claim 12, wherein a positive pressure is also applied along the umbilical cord or exit vessel.

14. The apparatus according to claim 12, wherein pressure is applied to the outside of the tissue with the application of negative pressure or suction in a region for connection of the umbilical cord or outflow vessel.

15. The apparatus according to claim 2, wherein said elastic membrane and said frame are shaped so that in a closed position the elastic membrane lies proximate to the tissue but does not compress said tissue directly.

16. The apparatus according to claim 1, wherein the tissue is confined in a partially or fully hermetic container.

17. The apparatus according to claim 16, wherein said hermetic container has an absorbent internal surface and an impermeable outer surface.

18. The apparatus according to claim 1, wherein pressure is applied to the tissue by a closed chamber surrounding a container adapted to connect to an umbilical cord or fluid outflow vessel by means of a system which seals the chamber from the outside environment.

19. An apparatus for extracting fluids from a body tissue having an aperture, comprising a seat adapted to position the tissue, and a pressure means for applying pressure to said tissue while leaving said tissue aperture open for the exit of said fluids, wherein said pressure means comprises at least one elastic membrane, said elastic membrane being stretched on a rigid supporting frame, said rigid supporting frame being hinged to a case body adapted to contain said pressure means; said frame being adapted to be left open in an inactive position, at right angles to a supporting surface adapted to support the tissue, or closed, in an active position, parallel to the supporting surface; wherein, in said closed position, a plane for connecting the membrane to the frame reaches beyond a protrusion profile of the tissue that rests on the supporting surface, thus leaving a central part of the elastic membrane free to act on said tissue and thus deform and compress the tissue, so that the tissue protrudes from the supporting surface to a different extent, and wherein the supporting surface has raised portions.

20. The apparatus according to claim 18, wherein said rigid frame is coupled to the elastic membrane so as to delimit a hermetically closed space, which is connected to a pressure system for applying pressure inside said space.

21. The apparatus according to claim 18, wherein said elastic membrane and said frame are shaped so that in the closed position the elastic membrane lies proximate to the tissue but does not compress said tissue directly.

22. The apparatus according to claim 19, wherein said pressure means comprises a plurality of membranes adapted to substantially surround the tissue.

23. The apparatus according to claim 19, wherein the supporting surface is constituted by a circular flat surface which has a central hole whose size is suitable for the passage of a tissue vessel for draining fluids.

24. The apparatus according to claim 23, further comprising a container for connecting to said vessel for collecting the fluid, so as to form a closed collection system which allows transfer of the fluid from the tissue to the collection container by means of a closed system.

25. The apparatus according to claim 19, wherein at least a portion of the supporting surface is shaped substantially as a cone, so that an apex of the cone is directed downward and a base of the cone delimits the supporting surface of the tissue; the apex being constituted by a hollow cylinder in order to allow passage of an umbilical cord of a placenta or of a vessel for the drainage of fluids from the placenta or organ or tissue; the supporting surface being provided so as to avoid producing obstructions or collapse of surface vessels of the placenta or organ or tissue, so as to avoid hindering flow of blood or fluid.

26. The apparatus according to claim 25, wherein the supporting surface has ridges which have a substantially spiral shape and start in a central region of the cone, proximate to a beginning of the cylindrical or hollow part.

27. The apparatus according to claim 19, wherein the supporting surface is free to rotate about a central axis.

28. The apparatus according to claim 19, wherein the supporting surface has balls or cams which are fixed to the supporting surface, below a portion of the pressure means and can rotate freely about their own axis; said balls or cams being moved by friction between a surface of the balls or cams and said portion of the pressure means.

29. The apparatus according to claim 19, wherein the pressure is also applied in a connecting part between a supporting membrane and a cylinder for containing an umbilical cord or outflow vessel for fluids and along said cylinder for containing the outflow vessel.

30. The apparatus according to claim 29, wherein a positive pressure is also applied along the umbilical cord or outflow vessel.

31. The apparatus according to claim 29, wherein pressure is applied to the outside of the tissue with the application of negative pressure or suction in a region for connection of the umbilical cord or outflow vessel.

32. The apparatus according to claim 19, wherein an at least partially hermetic container is provided to confine the tissue.

33. The apparatus according to claim 32, wherein said hermetic container has absorbent internal surface and an impermeable outer surface.

34. The apparatus according to claim 19, wherein pressure is applied to the tissue by a closed chamber surrounding a container adapted to connect to an umbilical cord or fluid outflow vessel by means of a system which seals the chamber from the outside environment.

35. An apparatus for extracting fluids from a body tissue having an aperture, the apparatus comprising a seat for positioning said tissue; a pressure means adapted to apply pressure to the tissue while leaving said tissue aperture open for the exit of said fluids, wherein said pressure means comprises at least one elastic membrane; and an at least partially hermetic container adapted to support the tissue, said hermetic container having an absorbent internal surface and an impermeable outer surface.

36. The apparatus according to claim 35, wherein said elastic membrane is stretched on a rigid supporting frame.

37. The apparatus according to claim 36, wherein said rigid supporting frame is hinged to a case body adapted to contain said pressure means; said frame being adapted to be left open in an inactive position, at right angles to a supporting surface adapted to support the tissue, or closed, in an active position, parallel to the supporting surface; wherein in said closed position, a plane for connecting the elastic membrane to the frame reaches beyond a protrusion profile of the tissue that rests on the supporting surface, thus leaving a central part of the elastic membrane free to act on said tissue and thus deform and compress the tissue, so that the tissue protrudes from the supporting surface to a different extent.

38. The apparatus according to claim 37, wherein said rigid frame is coupled to the elastic membrane so as to delimit a hermetically closed space, which is connected to a pressure system for applying pressure inside said closed space.

39. The apparatus according to claim 37 wherein the supporting surface is constituted by a circular flat surface which has a central hole whose size is suitable for the passage of a tissue vessel for draining fluids.

40. The apparatus according to claim 39, further comprising a connector adapted to connect to said vessel and a container adapted to collect the fluid, so as to form a closed collection system which allows transfer of the fluid from the tissue to the container by means of a closed system.

41. The apparatus according to claim 37, wherein at least a portion of the supporting surface is shaped as a funnel or cone, so that an apex of the cone is directed downward and a base of the cone delimits the supporting surface; the apex being constituted by a hollow cylinder in order to allow the passage of an umbilical cord of a placenta or of a vessel for the drainage of fluids from the placenta or organ or tissue; the supporting surface being provided so as to avoid producing obstructions or collapse of surface vessels of the placenta or organ or tissue, so as to avoid hindering flow of blood or fluid.

42. The apparatus according to claim 41, wherein the supporting surface has ridges which have a substantially spiral shape and start in a central region of the cone, proximate to a beginning of a cylindrical or hollow part.

43. The apparatus according to claim 37, wherein the supporting surface is free to rotate about a central axis.

44. The apparatus according to claim 37, wherein the supporting surface has raised portions.

45. The apparatus according to claim 37, wherein the supporting surface has balls or cams which are fixed to the supporting surface, below a portion of the pressure means and can rotate freely about their own axis; said balls or cams being moved by friction between a surface of the balls or cams and the portion of the pressure means.

46. The apparatus according to claim 37, wherein pressure is applied in a connecting part between the supporting surface and a cylinder for containing the umbilical cord or outflow vessel for fluids and along said cylinder for containing the outflow vessel.

47. The apparatus according to claim 46, wherein a positive pressure is applied along the umbilical cord or outflow vessel.

48. The apparatus according to claim 46, wherein pressure is applied to an outside of the tissue with application of negative pressure or suction in a region for connection of the umbilical cord or outflow vessel.

49. The apparatus according to claim 36, wherein said elastic membrane and said frame are shaped so that in the closed position the membrane lies proximate to the tissue but does not compress said tissue directly.

50. The apparatus according to claim 35, wherein said pressure means comprises a plurality of membranes adapted to substantially surround said tissue.

51. The apparatus according to claim 35, wherein pressure is applied to the tissue by a closed chamber surrounding a container adapted to connect to an umbilical cord or fluid outflow vessel by means of a system which seals the chamber from the outside environment.

52. An apparatus for extracting fluids from a body tissue having an aperture, comprising a seat for positioning the tissue, and a pressure means adapted to apply pressure to the tissue while leaving a tissue aperture open for the exit of the fluids, wherein said pressure means comprises at least one elastic membrane stretched on a rigid supporting frame, said rigid supporting frame being hinged to a case body adapted to contain said pressure means; said frame being adapted to be left open in an inactive position, at right angles to a supporting surface adapted to support the tissue, or closed, in an active position, parallel to the supporting surface; wherein, in said closed position, the plane for connecting the membrane to the frame reaches beyond a protrusion profile of the tissue that rests on the tissue supporting surface, thus leaving a central part of the membrane free to act on said tissue and thus deform and compress the tissue, so that the tissue protrudes from the supporting surface to a different extent; wherein at least a portion of the supporting surface is shaped as a funnel or cone, so that an apex of the cone is directed downward and a base of the cone delimits the supporting surface of the tissue; the apex being constituted by a hollow cylinder in order to allow passage of an umbilical cord of a placenta or of a vessel for drainage of fluids from a placenta or organ or tissue; the supporting surface being provided so as to avoid producing obstructions or collapse of the surface vessels of the placenta or organ or tissue, so as to avoid hindering the flow of blood or fluid; and wherein the supporting surface has ridges which have a substantially spiral shape and start in a central region of the cone, proximate to a beginning of the cylindrical or hollow part.

53. The apparatus according to claim 52, wherein said rigid frame is coupled to the elastic membrane so as to delimit a hermetically closed space, which is connected to a pressure system for applying pressure inside said space.

54. The apparatus according to claim 52, wherein said elastic membrane and said frame are shaped so that in the closed position the elastic membrane lies proximate to the tissue but does not compress said tissue directly.

55. The apparatus according to claim 52, wherein said pressure means comprises a plurality of membranes adapted to substantially surround said tissue.

56. The apparatus according to claim 52, wherein the supporting surface is constituted by a circular flat surface which has a central hole whose size is suitable for the passage of a tissue vessel for draining fluids.

57. The apparatus according to claim 56, further comprising a connector adapted to connect to said vessel and a container adapted to collect the fluid, so as to form a closed collection system which allows transfer of the fluid from the tissue to the container by means of a closed system.

58. The apparatus according to claim 52, wherein the supporting surface is free to rotate about a central axis.

59. The apparatus according to claim 52, wherein the supporting surface has raised portions.

60. The apparatus according to claim 52, wherein the supporting surface has balls or cams which are fixed to the supporting surface, below a portion of the pressure means and can rotate freely about their own axis; said balls or cams being moved by friction between a surface of the balls or cams and said portion of the pressure means.

61. The apparatus according to claim 52, wherein pressure is applied in a connecting part between the supporting surface and a cylinder for containing an umbilical cord or outflow vessel for fluids and along said cylinder for containing the outflow vessel.

62. The apparatus according to claim 61, wherein a positive pressure is also applied along the umbilical cord or outflow vessel.

63. The apparatus according to claim 61, wherein pressure is applied to an outside of the tissue with application of negative pressure or suction in a region for connection of the umbilical cord or outflow vessel.

64. The apparatus according to claim 52 further comprising an at least partially hermetic container adapted to confine the tissue.

65. The apparatus according to claim 64, wherein said hermetic container has an absorbent internal surface and an impermeable outer surface.

66. The apparatus according to claim 52, further comprising a closed chamber and a container inside said chamber for connecting to said umbilical cord or fluid outflow vessel while said chamber is sealed from the outside environment.

* * * * *

UNITED STATES PATENT AND TRADEMARK OFFICE
CERTIFICATE OF CORRECTION

PATENT NO. : 6,491,682 B2
DATED : December 10, 2002
INVENTOR(S) : Valter Paderni It is certified that error appears in the above-identified patent and that said Letters Patent is hereby corrected as shown below:

Title page,
Item [30], Foreign Application Priority Data, delete "UD96A0161" and insert -- UD96A000161 --.
Item [57], ABSTRACT,
Line 1, delete "(1)";
Line 2, delete "(26)";
Line 3, delete "membranes (17,22)" and insert -- means --;
Line 5, delete "(23)";
Line 8, delete "(29)";
Line 9, delete "(22)".

Column 2,
Line 67, delete "he" and insert -- the --.

Column 4,
Line 65, after "part" insert -- 2 --; delete "here" and insert -- in --;
Line 66, delete "FIG." and insert -- FIGS. --; after "1" insert -- and 8 --.

Column 5,
Line 24, after "part" insert -- 3 --;
Line 25, after "herein" insert -- in --; delete "FIG." and insert -- FIGS. --; after "2" insert -- and 9 --;
Line 29, after "tube" insert -- 24 --;
Line 41, delete "FIG." and insert -- FIGS. --; after "5" insert -- and 10 --;
Line 49, delete "FIG." and insert -- FIGS. --; after "6" insert -- and 11 --.

Column 6,
Line 33, after "support" insert -- 28 --;
Line 34, delete "28"; after "base" insert -- 29 --;
Line 35, delete "29";
Line 36, delete "30";
Line 64, after "part", insert -- 2 --;
Line 65, delete "allows" and insert -- allow --.

Column 7,
Line 12, after "spiral" insert -- 25 --;
Line 13, delete "26" and insert -- 23 --.

Column 8,
Lines 60 and 64, delete "18" and insert -- 19 --.

UNITED STATES PATENT AND TRADEMARK OFFICE
CERTIFICATE OF CORRECTION

PATENT NO.   : 6,491,682 B2
DATED        : December 10, 2002
INVENTOR(S)  : Valter Paderni It is certified that error appears in the above-identified patent and that said Letters Patent is hereby corrected as shown below:

Column 9,
Line 52, after "has" insert -- an --.

Column 12,
Line 24, delete "the" and insert -- a --;
Line 25, delete "surface" and insert -- membrane --.

Signed and Sealed this

Fifth Day of August, 2003

JAMES E. ROGAN
*Director of the United States Patent and Trademark Office*